United States Patent [19]
de la Rama et al.

[11] Patent Number: 5,951,471
[45] Date of Patent: Sep. 14, 1999

[54] CATHETER-BASED CORONARY SINUS MAPPING AND ABLATION

[75] Inventors: Alan de la Rama, Cerritos; Hosheng Tu, Tustin, both of Calif.

[73] Assignee: Irvine Biomedical, Inc., Irvine, Calif.

[21] Appl. No.: 09/037,282

[22] Filed: Mar. 9, 1998

[51] Int. Cl.[6] .............................. A61B 5/042; A61N 1/05
[52] U.S. Cl. ...................... 600/381; 600/374; 606/41; 607/99; 607/122
[58] Field of Search .................................. 600/374, 375, 600/381; 606/41; 607/99, 122

[56] References Cited

U.S. PATENT DOCUMENTS

| | | | |
|---|---|---|---|
| 5,445,148 | 8/1995 | Jaraczewski et al. | 600/374 |
| 5,549,581 | 8/1996 | Lurie et al. | 600/374 |
| 5,716,389 | 2/1998 | Walinsky et al. | 600/374 |

FOREIGN PATENT DOCUMENTS 2516848  10/1976  Germany ................................ 607/122

*Primary Examiner*—Lee Cohen

[57] ABSTRACT

A catheter-based method for coronary sinus mapping, pacing, and ablation, wherein a flexible electrode catheter, having a tip electrode with suspension structure, is pre-shaped to snugly fit into the coronary sinus, so that the tip electrode is positioned into the sinus; the distal section is deflected to expose a predetermined plurality of electrodes; and RF energy is then applied to the coronary sinus tissue through the electrodes to cause activation mapping, and/or ablation.

5 Claims, 7 Drawing Sheets

SECTION A-A

CATHETER-BASED CORONARY SINUS MAPPING AND ABLATION

FIELD OF THE INVENTION

The present invention generally relates to a medical device and its use for endocardiac mapping and ablation. More particularly, this invention relates to a catheter and the methods for coronary sinus mapping as a diagnostic device, and for coronary sinus ablation in the treatment of atrial flutter indications.

BACKGROUND OF THE INVENTION

Symptoms of abnormal heart rhythms are generally referred to as cardiac arrhythmias, while an abnormally rapid rhythm is referred to as a tachycardia. The present invention is concerned with the diagnosis and treatment of tachycardias, which are frequently caused by the presence of an "arrhythmogenic region" or an "accessory atrioventricular pathway" close to the inner surface of the atrium of a heart. The heart includes a number of normal pathways, which are responsible for the propagation of electrical signals from the upper chamber to the lower chamber, and which are necessary for performing normal systole and diastole function. The presence of an arrhythmogenic region or an accessory pathway in the atria can bypass or short circuit the normal pathway, potentially resulting in very rapid heart contractions, referred to here as atrial flutter. Atrial flutter is generally characterized by a saw tooth pattern with negative deflections in inferior leads of the ECG, while the atrial rate is in the range of 240–340 beats per minute.

Treatment of atrial flutter may be accomplished by a variety of approaches, including drugs, surgery, implantable pacemakers/defibrillators, and catheter ablation. While drugs may be the choice of treatment for many patients, they only mask the symptoms and do not cure the underlying causes, and they may also cause side effects. Implantable devices only correct the arrhythmia after it occurs. Surgical and catheter-based treatments, on the other hand, will actually cure the problem, usually by ablating the abnormal arrhythmogenic tissues or the accessory pathways responsible for the tachycardia.

There are, however, several drawbacks of the current mapping catheter as a device to assist in locating areas of aberrant electrical conduction for the catheter-based ablation of coronary sinus. One of the major problems lies in the unstable positioning of the catheter inside the right atrium of the heart. When a catheter is not stabilized, the heart's electrical conduction pattern is difficult to map and establish.

Therefore there is a need for an improved catheter, for improved methods in coronary sinus mapping as a diagnostic device, and for improved coronary sinus ablation in the treatment of atrial flutter and atrial fibrillation indications.

SUMMARY OF THE INVENTION

In general, it is an object of the present invention to provide a catheter and a catheter-based method that is used for mapping, pacing, and ablation of the coronary sinus. It is another object of this invention to provide a method for mapping, pacing, and ablation of the coronary sinus, using a catheter comprised of a plurality of electrodes, a pre-shaped tip section having an appropriate transition angle, and an appropriate length of the pre-shaped tip section. The "transition angle" is defined as the angle of the catheter shaft where the distal section protrudes from a catheter plane, wherein the catheter plane is the one formed by the deflected catheter. In one embodiment, the appropriate length of the pre-shaped tip section is preferably 20 to 40 cm. The "length of the pre-shaped tip section" is the length of the catheter shaft from the point of the beginning of the transition angle to the distal end of the catheter shaft. In another embodiment, the number of electrodes is preferably more then twenty. And yet, in still another embodiment, a reference electrode, which is one of the above-mentioned electrodes, is located about 30–40 cm from the distal tip of the catheter, wherein the reference electrode is to be positioned at the wall of the inferior vena cava.

A catheter of this invention for mapping the electrical conduction pattern of the coronary sinus in the right atrium of the heart comprises: a tubular elongate having a tip section, a distal end, a proximal end, and at least one lumen extending therebetween, wherein a plurality of band electrodes is disposed of on the tip section; a pre-shaped tip section having an appropriate transition angle; an appropriate length of the pre-shaped tip section; a handle means attached to the proximal end of the tubular elongate; a steerable mechanism located at the handle means, wherein the steering mechanism is to cause at least one deflection for the tip section; and a tip electrode having a suspension means, wherein the tip electrode is disposed at the distal end of the tubular elongate, and wherein the tip electrode moves and rebounds axially.

These objects, as well as others, are further provided in a method for the mapping and the pacing of the coronary sinus in the right atrium of the heart comprising of the steps: a) inserting a catheter into the right atrium of the heart, the catheter having a plurality of band electrodes, a pre-shaped tip section having an appropriate transition angle, and an appropriate length of the pre-shaped tip section; b) deflecting the tip section inside the right atrium, wherein the inferior vena cava wall and the upper right atrium wall are used as anchoring points for the catheter to stabilize the catheter tip on the coronary sinus; c) exposing the electrodes to the endocardial tissues around the coronary sinus; and d) mapping the endocardial surface, including the coronary sinus site, wherein the mapped electrical conduction pattern is used to assist in locating the areas of Currant electrical conduction, and to assist the catheter-based ablation of atrial flutter indications.

In another embodiment, RF energy is applied to the tissue surrounding the predetermined number of electrodes of the catheter of this invention to effect the ablation of the coronary sinus.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
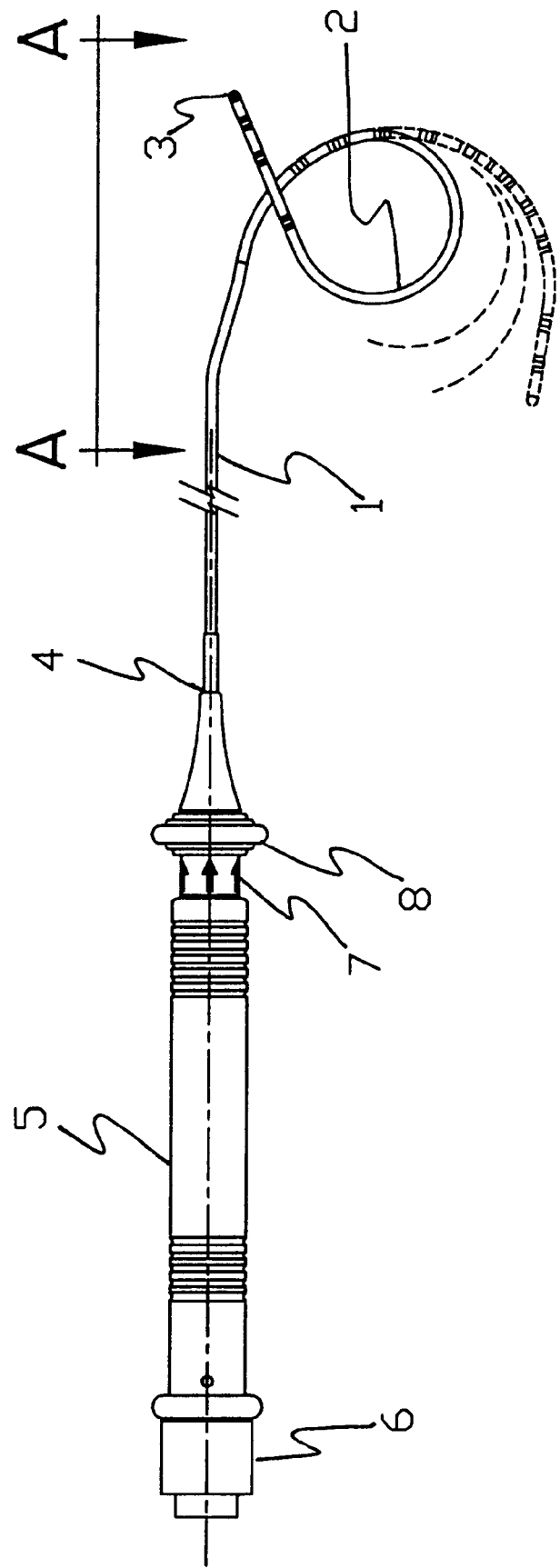
FIG. 1 is an overall view of a catheter system, having a pre-shaped distal section and a suspension tip electrode at its distal end, constructed in accordance with the principles of the present invention.

FIG. 1 shows an overall view of the catheter system having a pre-shaped distal section and a tip electrode at its distal end. A catheter system constructed in accordance with the principles of the present invention comprises: a tubular elongate shaft 1 having a distal tip section 2, a distal end 3, a proximal end 4, and at least one lumen extending therebetween. A handle 5 is attached to the proximal end 4 of the tubular elongate 1.

A connector 6 is secured at the proximal end of the handle 5, wherein the handle 5 has one steering mechanism 7. The steering mechanism 7 is to deflect the tip section 2 of the tubular elongate 1 for catheter maneuvering and positioning inside the coronary sinus of the right atrium. By pushing the plunger 8 of the handle 5 forward, the tip section of the tubular elongate deflects to one direction. The catheter plane formed by the distal tip section of the catheter system at this time is referred to herein as the "original catheter plane". By pulling back the plunger 8, the tip section returns to its neutral position or deflects to the opposite direction. In another embodiment, the steering mechanism 7 at the handle 5 comprises a means for providing a plurality of deflectable curves on the distal tip section 2 of the tubular elongate.

Figure 2:
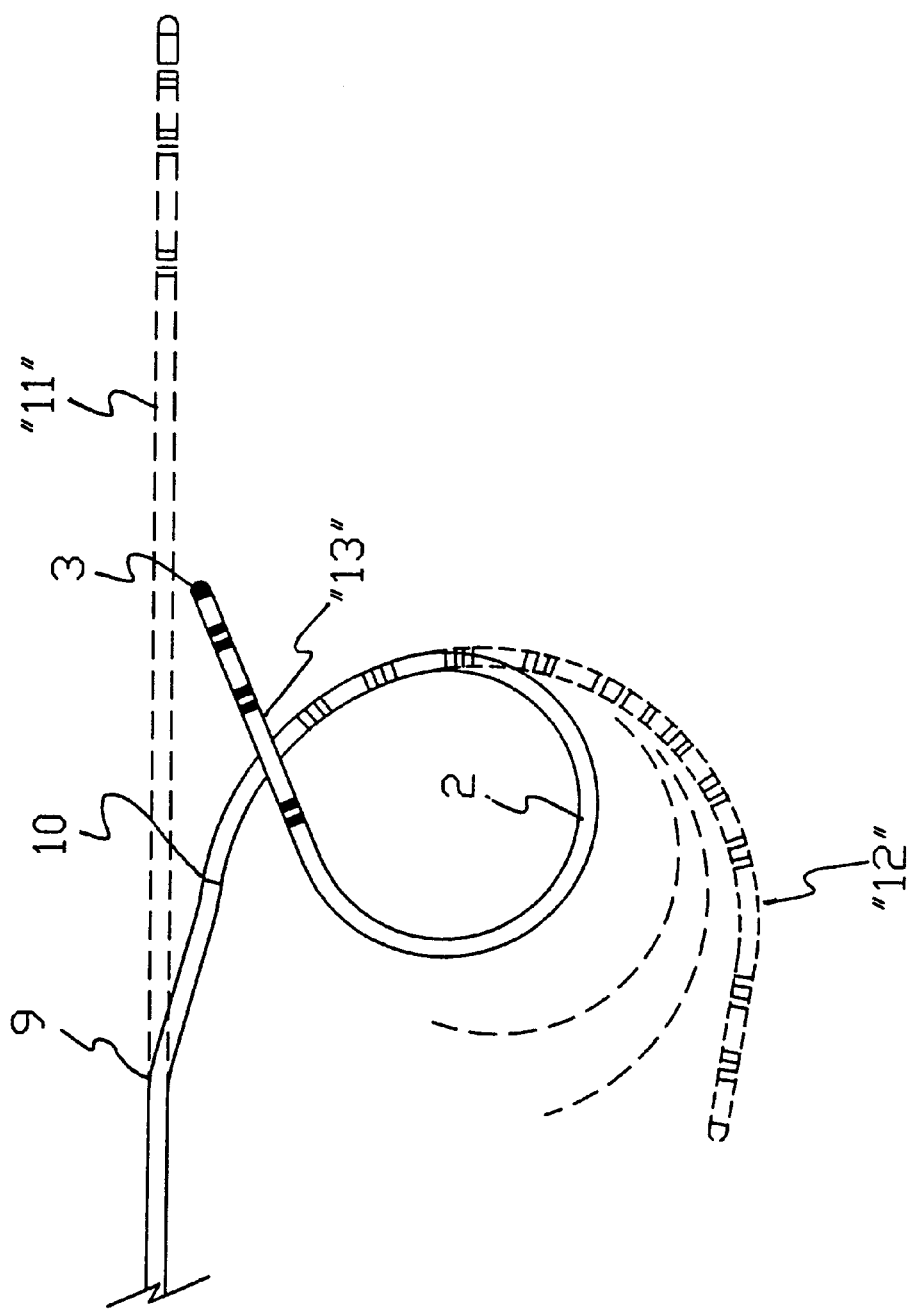
FIG. 2 is a close-up view of the distal section of the catheter system comprising a steering capability.

FIG. 2 shows a close-up view of the distal section of the catheter system comprising steering capability. In one embodiment, the proximal region of the tip section 2 includes special pre-shaped curving, to position the catheter at the entrance rim of the inferior vena cava into the right atrium. The special pre-shaped curving has a "transition angle" of more than 30 degrees, preferably in the range of 40 to 50 degrees. The "transition angle" is defined as the angle of the catheter shaft where the distal section protruded from an original catheter plane, wherein the original catheter plane is formed by the deflected catheter. The proximal region of the special pre-shaped curving starts at point 9 and ends at point 10, which is referred to as the "transition range". The "transition range" is typically 2 to 5 cm long. The "length of the pre-shaped tip section" is the length of the catheter shaft from the point of the transition angle 9, to the distal end 3, of the catheter system. In one embodiment, the appropriate length of the pre-shaped tip section is preferably 20 to 40 cm long. The region, including the transition angle point and its subsequent length, is specifically designed for the purpose of stabilizing the catheter of this invention during electrophysiology study. The distal section 2 of the catheter system is deflectable. When introducing the catheter into the heart chamber, the tip section is deflected as pattern "11" in FIG. 2. When the catheter is located inside the right atrium, the tip section is deflected as pattern "12" in FIG. 2, while pattern "13" is deployed by positioning the tip of the catheter system inside the coronary sinus.

Figure 3:
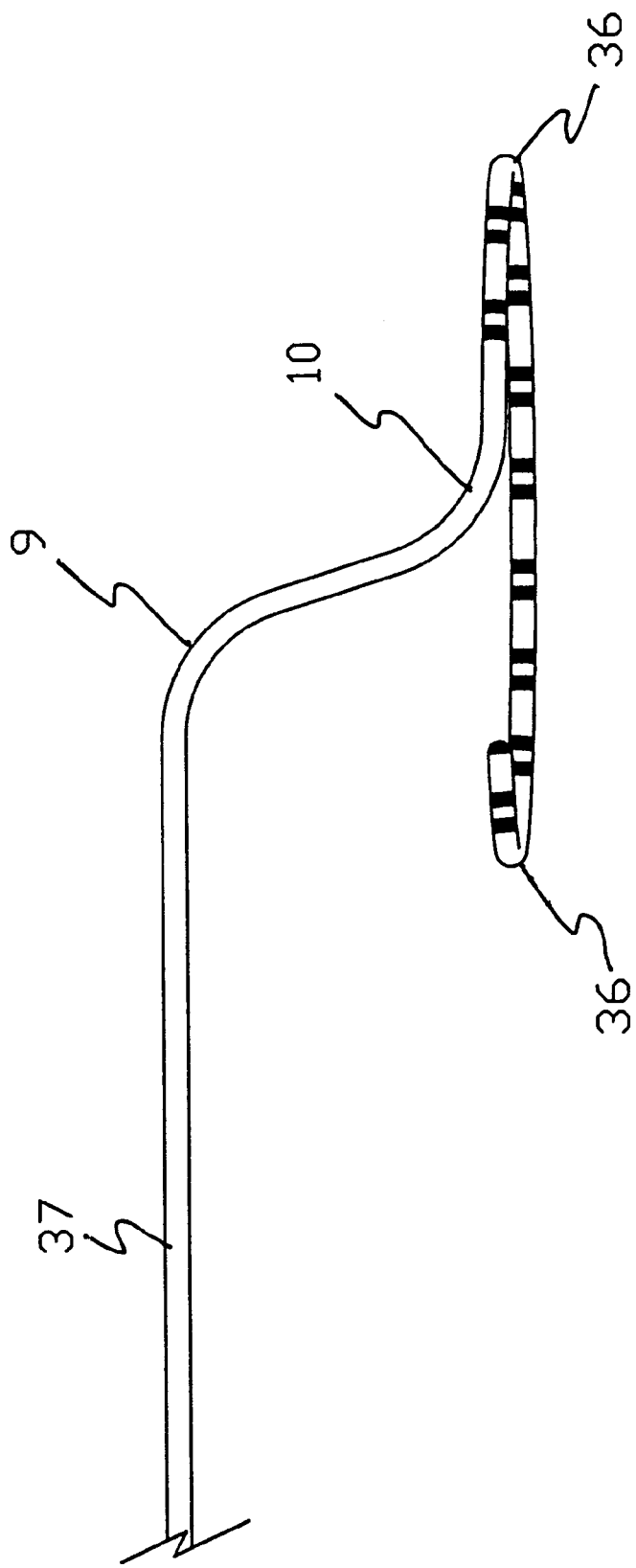
FIG. 3 is close-up view of the distal section of the catheter system including the transition angle, section A—A of FIG. 2.

FIG. 3 is close-up view of the distal section of the catheter system including the transition range, section A—A of FIG. 1. The transition range starts from point 9 and ends at point 10. The "original catheter plane" 36—36 is parallel to the proximal section of the catheter shaft 37. Without the transition range, the "original catheter plane" would have lain on the same catheter plane when it is being deflected.

Figure 4:
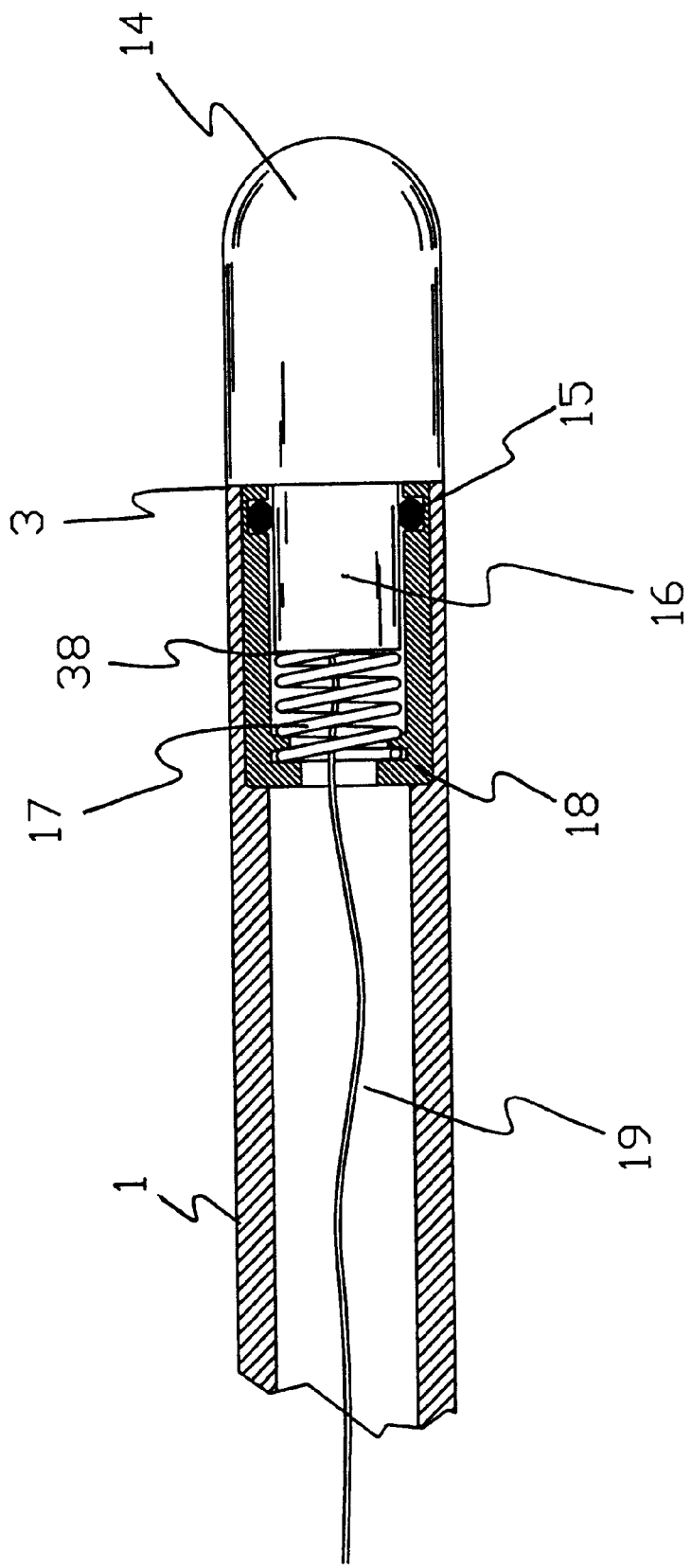
FIG. 4 is a close-up view of the distal section of a catheter system comprising a spring type support for the tip electrode.

FIG. 4 shows a close-up view of the distal section of the catheter system comprising a spring-type support for the suspensional tip electrode. The tip electrode 14 is disposed at the distal end 3 of the tubular elongate 1. The tip electrode 14 is supported by at least an O-ring 15, which stays within a groove around the stem 16 of the tip electrode 14. This O-ring 15 also serves as a barrier to prevent any blood or body fluid from backflowing into the lumen of the tubular elongate 1.

In one embodiment, one end of the spring-like coil 17 is secured to the proximal end 38 of the tip electrode 14, while the other end of the spring-like coil 17 is secured to or sits on a coil stopper 18. The coil stopper 18 is firmly secured to a predetermined point on the inside surface of the tubular elongate 1. The function of the coil stopper 18 is to provide a fixed baseline for the spring-like coil 17 to cause the tip electrode 14 to move forward and backward axially. A conducting wire 19 is connected to the tip electrode 14 for the purpose of transmitting the electrical signal from the tip electrode to an external EKG monitor.

Figure 5:
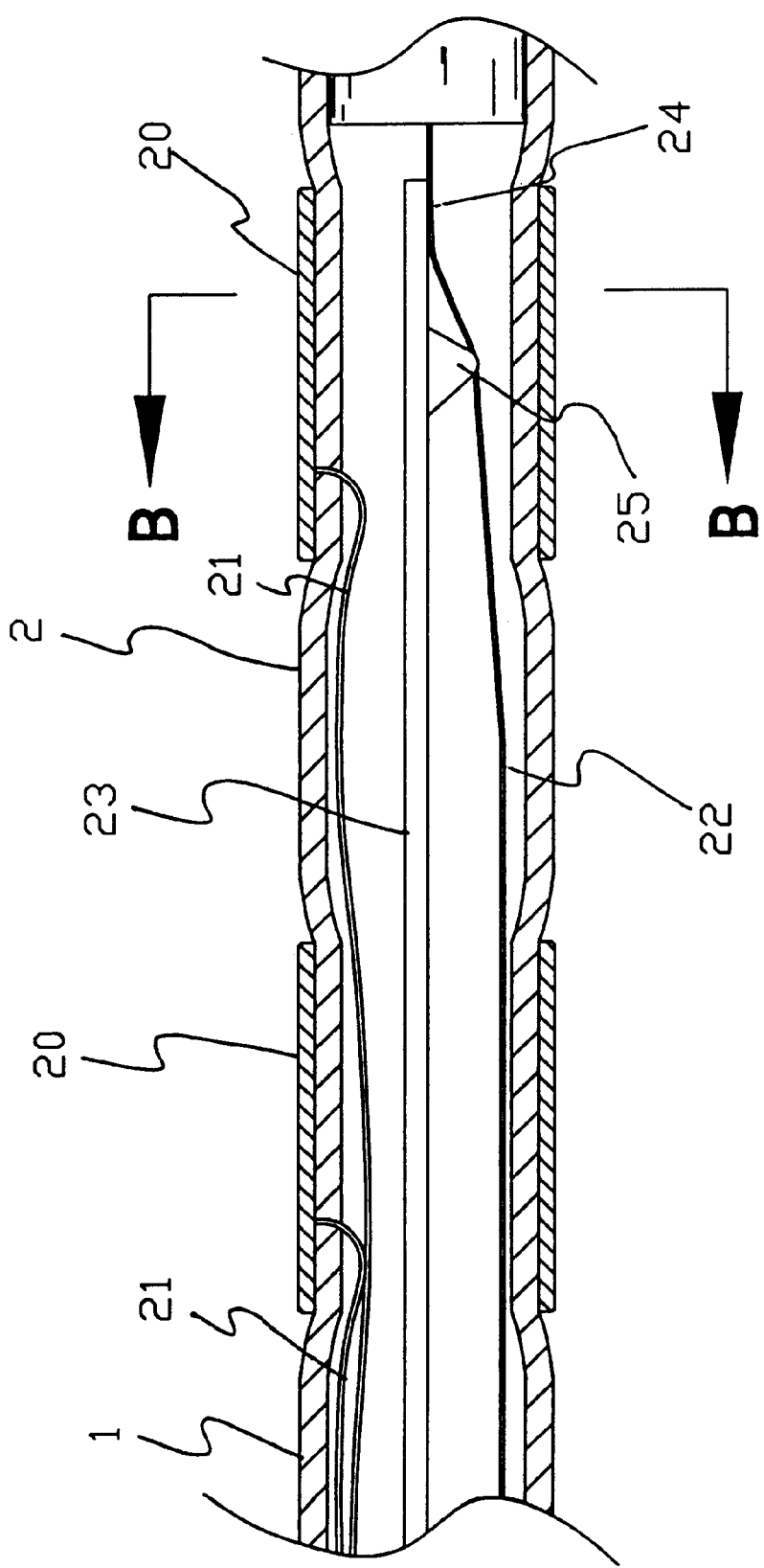
FIG. 5 is a close-up view of the distal section comprising a plurality of band electrodes and a wiring setup for the steering mechanism of this invention.

FIG. 5 shows a close-up view of the distal section comprising a plurality of band electrodes and a wiring setup for the steering mechanism of this invention. A plurality of band electrodes 20 is disposed of on the tip section 2 of the tubular elongate 1. A conducting wire 21 is connected to each band electrode for transmitting the electrical signal from each band electrode to an external EKG monitor. A steering wire 22 is secured to a flat wire means 23 at a securing point 24 which is close to the distal end of the tip section 2. A tiny bump 25 is secured to the flat wire 23, where it provides a means of distancing the steering wire 22 away from that flat wire 23. This becomes more obvious when a bi-directional deflection mechanism is devised. In such a case, two steering wires are secured to the flat wire 23 while two tiny bumps are installed, one at each side of the flat wire, so that any of the two steering wires would never come in contact to the flat wire at the proximity of the securing point 24.

Figure 6:
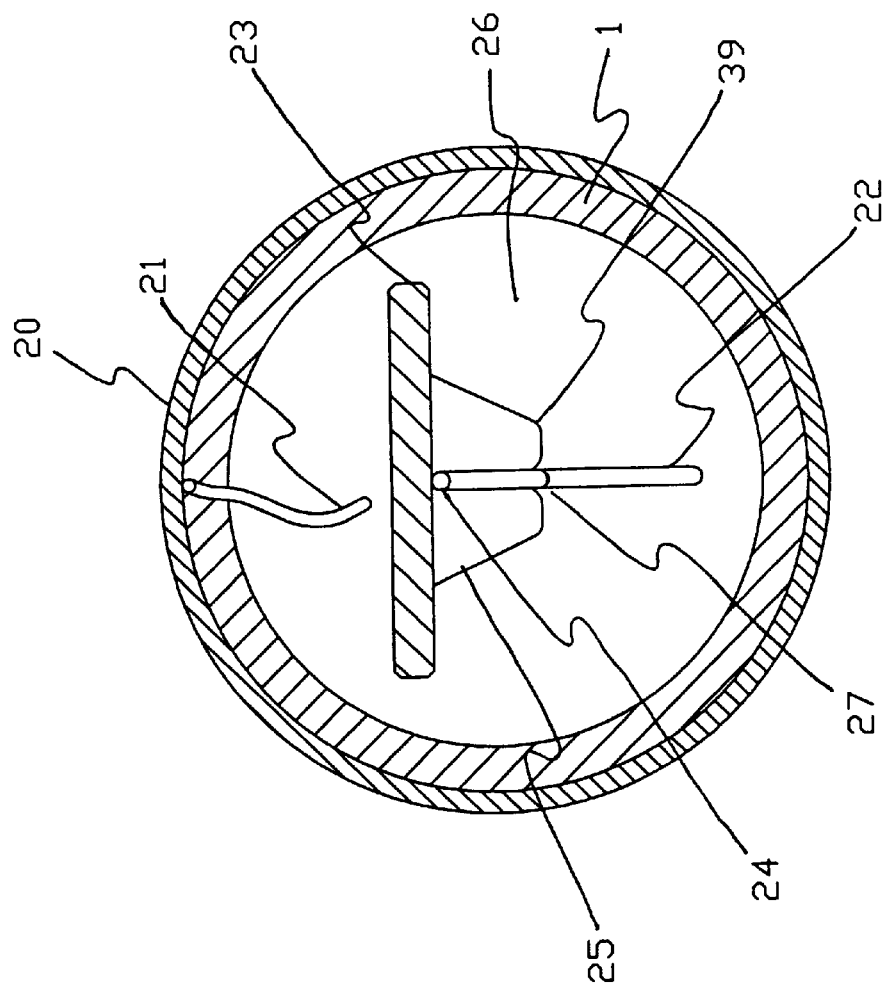
FIG. 6 is a cross-sectional view, section B—B, of FIG. 5.

FIG. 6 is a cross-sectional view, of FIG. 5, section B—B. The flat wire 23 and its corresponding steering wire 22 are located within the lumen 26 of the tubular elongate 1. The steering wire 22 is secured to the flat wire 23 at the securing point 24. The outer end 39 of the tiny bump 25 has a trough 27, which is used to confine the steering wire 22 to the top 39 of the tiny bump 25, when the steering wire 22 is in its relaxation state.

Figure 7:
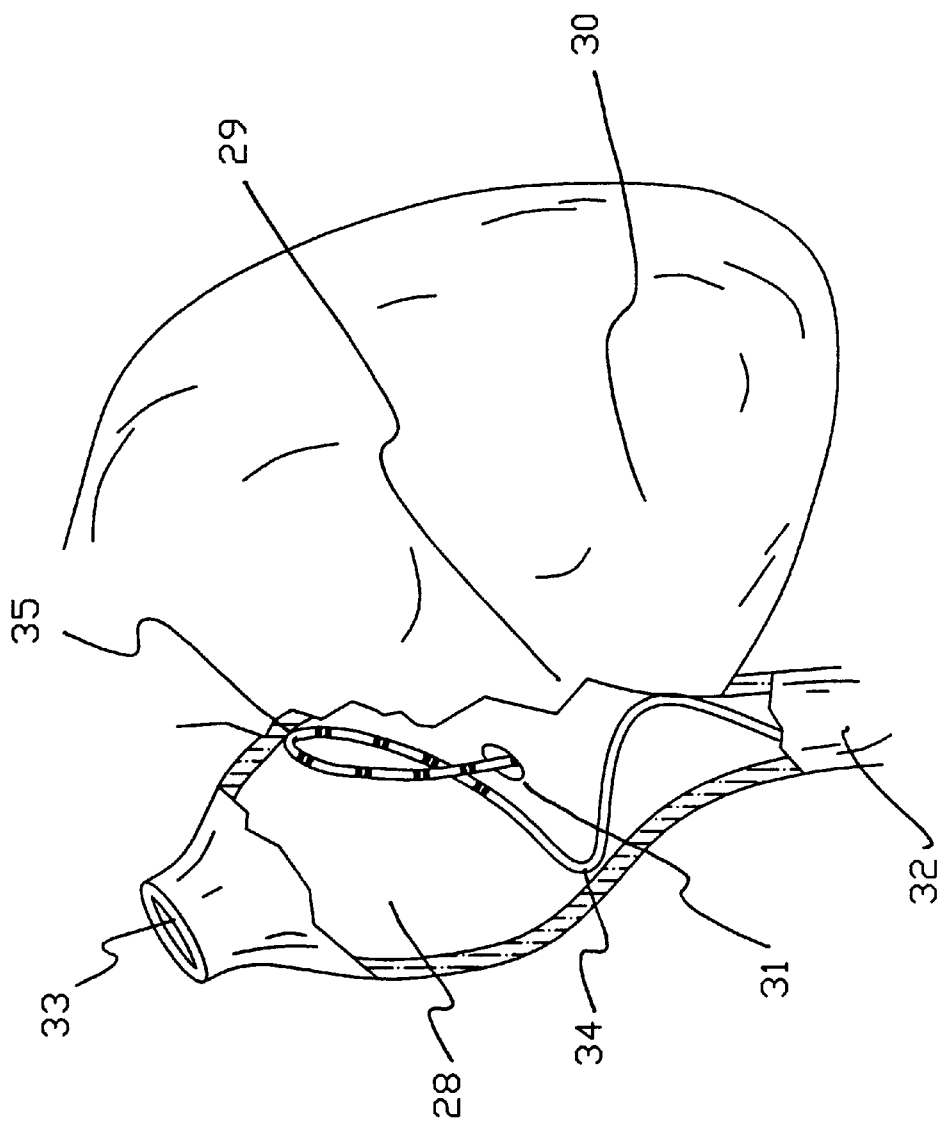
FIG. 7 is a perspective view of one of the methods of operations of the present invention.

FIG. 7 is a perspective view of one of the methods of use of the present invention. The blood flows from both the inferior vena cava 32 and the superior vena cava 33 to the right atrium 28 of the heart. The right atrium 28 is separated by a tricuspid valve 29 from the right ventricle 30. The coronary sinus 31 within the right atrium 28 provides an ideal anchoring point, along with two other anchoring points 34 and 35, to stabilize the catheter within the right atrium. The proper "transition angle" and the "transition range" ensure that the catheter system of the present invention is securely positioned inside the atrium for coronary sinus mapping and ablation.

A catheter of this invention is inserted into the right atrium 28 of the heart, the catheter having a plurality of electrodes, a pre-shaped tip section, and an appropriate length of the pre-shaped tip section. The tip section of the catheter is deflected inside the right atrium 28, wherein the inferior vena cava wall 34 and the high right atrium wall 35 are used as anchoring points to stabilize the catheter tip on the coronary sinus. Thereafter the electrodes are exposed to the endocardial tissues around the coronary sinus inside the right atrium. The tip electrode lies inside the coronary sinus to provide a third anchoring point.

The electrical conductance pattern is established by mapping the endocardial surface, including the coronary sinus site, where the mapped electrical conduction pattern is used to assist locating areas of aberrant electrical conduction, and to assist the catheter-based ablation of atrial flutter indications.

In another embodiment, RF energy is applied to the tissue surrounding the predetermined number of electrodes of the catheter of this invention to effect the ablation of coronary sinus. The electrodes are formed of conducting materials selected from the group consisting of platinum, iridium, gold, silver, stainless steel, Nitinol, or an alloy of their mixture.

In a further embodiment, a temperature sensor, either a thermocouple means or a thermister means, is constructed at the proximity of the electrode to measure the tissue contact temperature when RF energy is delivered. The temperature sensing wire from the thermocouple means or thermister means is connected to one of the contact pins (not shown) of the connector 6, and externally connected to a transducer, as well as to a temperature controller. The temperature reading is thereafter relayed to a closed-loop control mechanism to adjust the RF energy output. The RF energy delivered is thus controlled by the temperature sensor reading or by a pre-programmed control algorithm.

From the foregoing, it should now be appreciated that an improved catheter system having a plurality of electrodes, a pre-shaped tip section for stabilizing the catheter inside the right atrium, and a tip electrode comprising of a suspension means, and a method of use, have been disclosed for coronary sinus mapping and/or ablation. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter for mapping the electrical conduction pattern of the coronary sinus in the right atrium of the heart comprising:

an elongate tubular element having a pre-shaped tip section, a distal end, a proximal end, and at least one lumen extending therebetween, wherein a plurality of band electrodes is disposed on the tip section; and wherein the pre-shaped tip section has an appropriate transition angle and length;

a handle attached to the proximal end of the elongate tubular element;

a steering mechanism located at the handle, wherein the steering mechanism is to cause at least one deflection for the tip section; and a tip electrode disposed at the distal end of the elongate tubular element, wherein the tip electrode comprises suspension means for coupling the tip electrode to the distal end of the elongate tubular element in a suspension manner, and wherein the tip electrode has capability of moving and rebounding axially.

2. The catheter for mapping the electrical conduction pattern of the coronary sinus in the right atrium of the heart as in claim 1, wherein the pre-shaped tip section has a transition angle of 40 to 50 degrees.

3. The catheter for mapping the electrical conduction pattern of the coronary sinus in the right atrium of the heart as in claim 1, wherein the length of the pre-shaped tip section of the elongate tubular element is longer than 20 cm.

4. The catheter for mapping the electrical conduction pattern of the coronary sinus in the right atrium of the heart of claim 1 further comprising a reference electrode, wherein the reference electrode is located about 30–40 cm from the distal end of the elongate tubular element.

5. The catheter for mapping the electrical conduction pattern of the coronary sinus in the right atrium of the heart as in claim 1, wherein the suspension means includes a coil at a proximal end of the tip electrode.

* * * * *